(12) United States Patent
Mohr

(10) Patent No.: US 6,217,712 B1
(45) Date of Patent: Apr. 17, 2001

(54) CATALYTIC SIMULATION USING RADIO FREQUENCY WAVES

(76) Inventor: Thomas J. Mohr, 48 Sandway Crescent, Maple, Ontario (CA), L6A 2M1

( * ) Notice: Subject to any disclaimer, the term of this patent is extended or adjusted under 35 U.S.C. 154(b) by 0 days.

(21) Appl. No.: 09/412,359

(22) Filed: Oct. 5, 1999

Related U.S. Application Data

(63) Continuation-in-part of application No. 08/760,342, filed on Dec. 4, 1996, now abandoned.

(51) Int. Cl.$^7$ .............................. C07C 1/00; B01J 37/34; C21D 1/04; G01V 3/00
(52) U.S. Cl. ......................... 204/157.15; 502/5; 502/20; 148/108; 324/300
(58) Field of Search ........................... 204/157.15; 502/5, 502/20; 148/108; 324/300

(56) References Cited

U.S. PATENT DOCUMENTS

| 5,797,876 | 8/1998 | Spears et al. | 604/95 |
|---|---|---|---|
| 5,893,838 | 4/1999 | Daoud et al. | 604/26 |
| 5,957,899 | 9/1999 | Spears et al. | 604/264 |
| 5,976,119 | 11/1999 | Spears et al. | 604/508 |
| 6,030,357 | 2/2000 | Daoud et al. | 604/26 |

FOREIGN PATENT DOCUMENTS

2046652 * 10/1995 (RU) .

OTHER PUBLICATIONS

Spears, J. Richard et al. "Reperfusion Microvascujar Ischemia Attenuated with Aqueous Oxygen Infusion in a Porcine Coronary Occulsion Model", Circulation Supplement I, vol. 100, NO. 18:1–512 Nov. 2, 1999.

Davis, SC et al. "Delivery of Oxygen to Cutaneous Tissue Via a Super Saturated Oxygen (SOS) Emulsion", The Journal of Investigative Dermatology, vol. 112, No. 4: 632, Apr. 1999.

Spears, J. Richrd et al. "Post MI Aqueous Oxygen Hyperoxemic Coronary Reperfusion Acutely Improves Canine LV Function Compared to Normoxemic Reperfusion", The American Journal of Cardiology TCT Abstracts Supplement vol. 82 (Supple 7A): 100S, TCT–277, Oct. 1998.

(List continued on next page.)

Primary Examiner—Edna Wong
(74) Attorney, Agent, or Firm—Parkhurst & Wendel, L.L.P.

(57) ABSTRACT

The invention relates to a method of using radio frequency waves to artificially create catalytic action in a catalyst-free chemical reaction within a substance. To mimic or imitate the catalyst, radio frequency waves are transmitted through the substance at a signal strength sufficient to electronically reproduce the effect of the physical presence of a selected catalyst. The radio frequency waves have a selected transmission frequency substantially equal to a catalyst signal frequency of the selected catalyst, defined as the signal frequency determined by nuclear magnetic resonance of the selected catalyst. It is commonplace to use nuclear magnetic resonance to identify elements within a substance and the signal frequencies of various elements (including catalysts) are listed in widely published tables. To date, the mechanism by which catalysts bring about chemical reactions has been unknown. The inventor has recognised that the physical presence of a catalyst brings about a chemical reaction due to the emission of low intensity radio frequency waves from the catalyst with the signal frequency that is emitted being the signal frequency of the catalyst that is commonly determined by nuclear magnetic resonance. Therefore, the invention can be used to eliminate the need for expensive metallic catalysts, such as platinum. The invention electronically reproduces the effect of the physical presence of a catalyst by transmission of a radio frequency wave with a signal frequency equal to that signal frequency emitted by the catalyst and as determined by nuclear magnetic resonance of the catalyst.

22 Claims, 2 Drawing Sheets

OTHER PUBLICATIONS

Schwartz, RS et al. "Coronary Reperfusion with Aqueous Oxygen Improves Left Ventricular Ejection Fraction and May Reduce Mortality in an Ischemic Porcine Model", The American Journal of Cardiology TCT Abstracts Supplement vol. 82 (Suppl 7A): 86S, TCT–231, Oct. 1998.

Cumberland, DC et al. "Assessment of the Safety and Efficacy of Supersaturated Oxygen Solution: A Novel Mthod Reducing Myocardial Ischaemia in PTCA", The American Journal of Cardiology CT Abstracts Supplement, vol. 82 (Suppl. 7A): 100S, TCT–276, Oct. 1998.

Spears, J. Richard et al. "Aqueous Oxygen: A Highly $O_2$ Supersaturated Infusate for Hyperoxemic Treatment of Postischemic Mycardium", American Journal of Cardiology, vol. 80, No. 70A: 72S, Oct. 1997.

Spears, J. Richard et al. "Hyperoxemic Perfusion with Aqueous Oxygen Improves Left Ventricular Function During Experimental MI Reperfusion" Circulation 1997, vol. 96, No. 8: 1–364, 1997. no month available.

Spears, J. Richard et al. "Aqueous Oxygen: A Highly $O_2$ Supersaturated Infusate for Regional Correction of Hypoxemia and Production of Hyperoxemia", Circulation 1997, vol. 96, No 12: 4385–4391, Dec. 16, 1997.

* cited by examiner

CATALYTIC SIMULATION USING RADIO FREQUENCY WAVES

REFERENCE TO RELATED APPLICATION

This application is a Continuation-in-Part application related to previously filed Ser. No. 08/760,342 filed Dec.4, 1996 entitled: Catalytic Resonance Simulator, also invented by Thomas J. Mohr, now abandoned.

TECHNICAL FIELD

The invention relates to a method of using radio frequency waves to artificially create catalytic action, in a catalyst-free chemical reaction within a substance, to mimic or imitate the physical presence of a catalyst, by transmitting radio frequency waves through the substance at a signal strength sufficient to electronically reproduce the effect of the physical presence of a selected catalyst.

BACKGROUND OF THE ART

Catalysts are used in many conventional chemical reactions frequently in the form of precious metals plated on metal anodes or cathodes, ceramic catalytic converter structures and the like. The catalysts are inert and are not consumed during the chemical reaction but their physical presence is required to carry out the reaction or enhance effectiveness. The actual mechanism by which a catalyst exerts influence on the chemical reaction is not known, however, the effect of the presence of various catalysts has been well established.

The disadvantage of using conventional catalysts is that the initial cost of such precious metals is very high, periodic cleaning or replacement is required to ensure maximum efficiency, and disposal of materials coated with catalysts involve catalyst reclaiming, high cost and possible heavy metal contamination. Minimal amounts of catalyst are used as a result of their high cost. The effectiveness of a catalyst is not controllable and the conventional manner of increasing the effect of a catalyst is to increase exposure to the catalyst during the chemical reaction.

It is an object of the present invention to artificially imitate the physical presence of a catalyst in a chemical reaction with electronics to minimise or eliminate the use of expensive catalytic materials and to avoid the above disadvantages of conventional catalyst use.

It is also desirable to control the effectiveness of the electronic means imitating the catalyst to exert an active influence in optimising the chemical reaction without the physical presence of a catalyst.

Further objects of the invention will be apparent from review of the disclosure and description of the invention below.

DISCLOSURE OF THE INVENTION

The invention relates to a method of using radio frequency waves to artificially create catalytic action in a catalyst-free chemical reaction within a substance. To mimic or imitate the catalyst, radio frequency waves are transmitted through the substance at a signal strength sufficient to electronically reproduce the effect of the physical presence of a selected catalyst. The radio frequency waves have a selected transmission frequency, substantially equal to a catalyst signal frequency of the catalyst, defined as the signal frequency determined by nuclear magnetic resonance of the selected catalyst.

It is commonplace to use nuclear magnetic resonance to identify elements within a substance and the signal frequencies of various elements (including catalysts) are listed in widely published tables.

To date, however, the exact mechanism by which catalysts bring about chemical reactions has been unknown. There is no doubt though that "inert" catalysts are essential for some chemical reactions to occur and can clearly optimise other chemical reactions, even though the catalyst is not consumed or altered during such reactions.

The inventor has recognised that the physical presence of a catalyst brings about a chemical reaction due to the emission of low intensity radio frequency waves from the catalyst. These emitted radio waves have a very low signal strength with a signal frequency equal to the signal frequency of the catalyst that is commonly determined by nuclear magnetic resonance and conventionally used to identify the catalyst.

Therefore, the invention relates to use of electronically generated radio frequency signals to imitate catalysts and eliminate the need for expensive metallic catalysts, such as platinum. The invention electronically reproduces the effect of the physical presence of a catalyst, by transmission of an artificially produced radio frequency wave signal with a signal frequency equal to the natural signal frequency emitted by the catalyst and as determined by nuclear magnetic resonance of the catalyst.

Although the drawings and related description of the invention concern a preferred embodiment applied to the example of a liquid electrolytic reaction within a conducting pipeline, it will be understood that the invention in it's broad scope includes application to any reaction in which the presence of a simulated catalyst is of benefit.

By providing an electronically simulated radio frequency transmission, which mimics the radio frequency transmission resulting from the physical presence of a selected catalyst, the use of an actual catalyst can often be completely eliminated. In some applications it may be preferable to retain the presence of conventional catalysts but to enhance the effectiveness of those catalysts present by adding a simulated radio frequency transmission of strength or amplitude equal or greater than the catalyst's own transmission. The costs of expensive plated precious metal catalysts can be minimised, and the costs of reclaiming and repairing various catalytic converters reduced.

Further details of the invention and its advantages will be apparent from the detailed description and drawings included below.

BRIEF DESCRIPTION OF THE DRAWINGS

In order that the invention may be readily understood, two preferred embodiments of devices which operate using the method of the invention and variations thereof will be described by way of example, with reference to the accompanying drawings wherein.

DETAILED DESCRIPTION OF PREFERRED EMBODIMENTS

Figure 1:
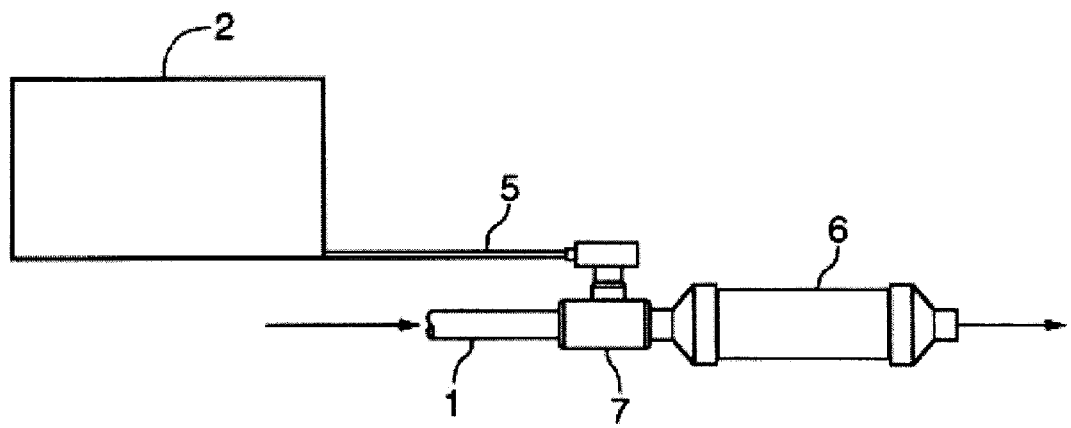
FIG. 1 is a schematic view of one embodiment of a device utilising the method of the invention applied to a liquid electrolyte reaction within a conducting pipeline housing an electrolytic cell, a submerged standing wave antennae and a radio frequency generator.

FIG. 1 illustrates a device which can be used to carry out the method of the invention. In this example, the method of the invention is used to artificially create catalytic action in a catalyst-free chemical reaction within a substance that is conducted through a pipeline in the direction of the arrows shown. Radio frequency waves are used to artificially create this catalytic action as liquid electrolyte is conveyed through a pipeline 1 in the direction of arrows by a pump (not shown). Electrolyte is used in this example, however it would be understood that any means for containing a substance during a chemical reaction may be used such as agitator tanks, cracking towers, settling tanks, etc.

Figure 2:
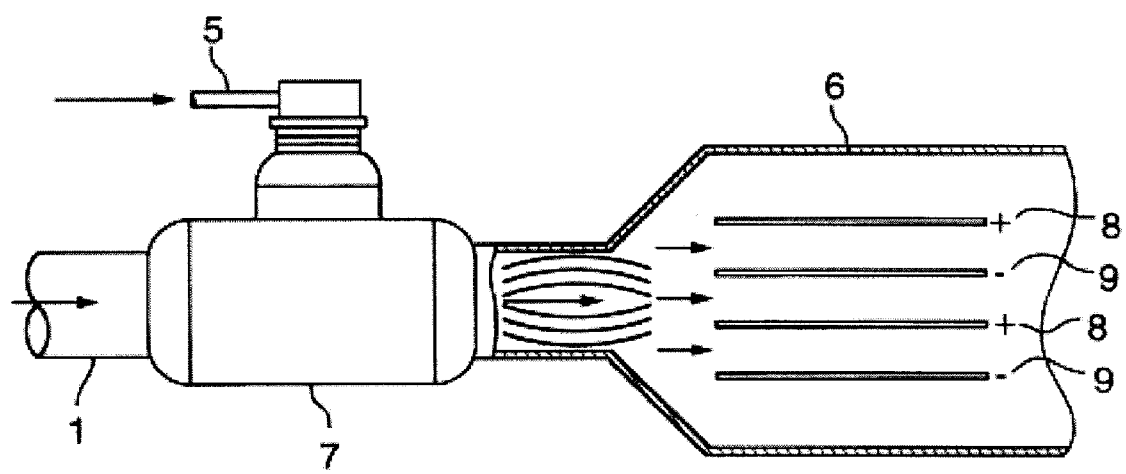
FIG. 2 is a partially longitudinal sectional detail view of the electrolytic cell and antennae housing.
Figure 3:
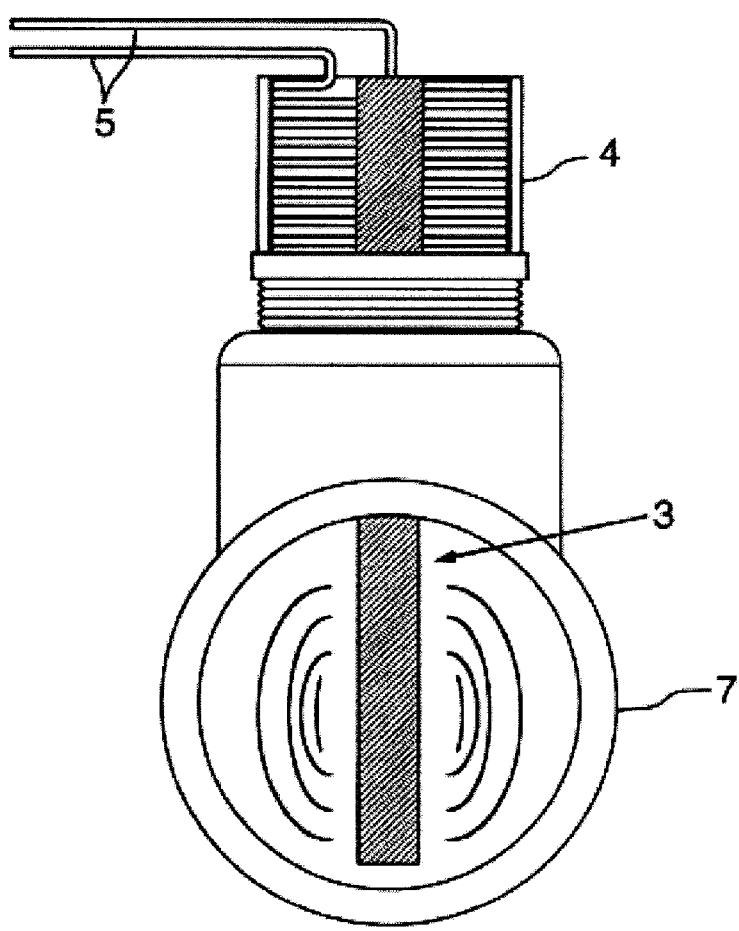
FIG. 3 is a sectional transverse view through the antennae housing showing the standing wave antennae and oscillator coil.

A radio frequency wave transmitter 2 is disposed in communication with the electrolyte by means of a standing wave antenna 3 which is submerged in the electrolyte within the pipe 1 and the section 7. As best shown in FIGS. 2 and 3, the antenna 3 communicates with an oscillator coil 4 which receives the radio frequency signal from the frequency generator 2 via a cable 5.

In the embodiment illustrated in FIGS. 1, 2, and 3, the chemical reaction is electrolysis carried out within an electrolytic cell 6. Within the cell 6 is disposed cathode 9 and anodes 8 both connected to a source of an electric current and immersed in the electrolytic substance. Preferably the electrolyte is water and the chemical reaction comprises electrolysis to increase the dissolved oxygen gas within the water as it passes through the electrolytic cell 6.

In operation, the method involves transmitting radio frequency waves generated from the frequency generator 2 and emitted via the standing wave antenna 3 to conduct the radio frequency waves through the electrolyte at a signal strength sufficient to electronically reproduce the effects of the physical presence of a catalysts.

In a traditional electrolysis reaction, the cathodes 9 and anodes 8 would be plated with a metallic catalyst such as platinum. However, in the method of the invention the cathodes 9 and anodes 8 are not plated with a catalyst since the radio frequency waves transmitted via the antenna 3 artificially create the same catalytic action. The radio frequency waves have a selected transmission frequency, substantially equal to a catalyst signal frequency of the selected catalyst. This catalyst signal frequency is defined as the signal frequency conventionally determined by nuclear magnetic resonance of the selected catalyst. For example, where the selected catalyst is platinum the radio frequency transmission is in the order of 9.29 megahertz. This frequency and the frequencies of other catalysts are commonly listed in NMR tables and are readily available to those skilled in the relevant art.

It will be understood however, that nuclear magnetic resonance is conventionally used to identify elements that are present within an unknown substance. The elements under bombardment of external radio frequencies in the presence of strong magnetic field emit a signal radio frequency which can be detected and definitely identifies the element. These signal frequencies are listed in NMR tables and are used by those skilled in the art to conclusively determine what elements are present within an unknown substance.

In contrast, the present invention utilises these established radio frequencies to electronically artificially create catalytic action in a catalyst free chemical reaction. Therefore, it will be understood that the method does not use conventional nuclear magnetic resonance but rather uses the result of NMR to determine the appropriate radio frequency to be used and transmitted through the antenna 3.

For example, if the catalyst which is necessary for a chemical reaction is uranium, iridium or ruthenium, the radio frequency transmitted from the frequency generator 2 and emitted by the antenna 3 is adjusted accordingly to match the radio frequency from NMR tables.

By experimentation, it has been concluded that the precise radio frequency to be transmitted through the substance may require slight variation to optimise the reaction, depending on the size and shape of the reaction chamber and other details of the physical containment of the chemical reaction. However, the range within which the frequency varies is relatively small. For example, if the NMR tables indicate that frequency for platinum is 9.29 megahertz, the variation in frequency in optimisation will be in the order of plus or minus 0.5 megahertz.

The radio frequency generator 2 can be used to fine-tune the transmission frequency while monitoring the reaction to optimise the reaction. For example, in the device shown in FIG. 1, the generation of oxygen gas within the water electrolyte can be monitored easily by using a dissolved oxygen meter downstream of the electrolytic cell 6. In addition, the method can include fine tuning the signal strength emitted by the frequency generator 2 while monitoring the reaction with the dissolved oxygen meter to optimise the reaction. Many chemical reactions also require the regulation of temperature to optimise the reaction and this step can be accomplished by conventional means such as chillers or heaters for the electrolyte.

Figure 4:
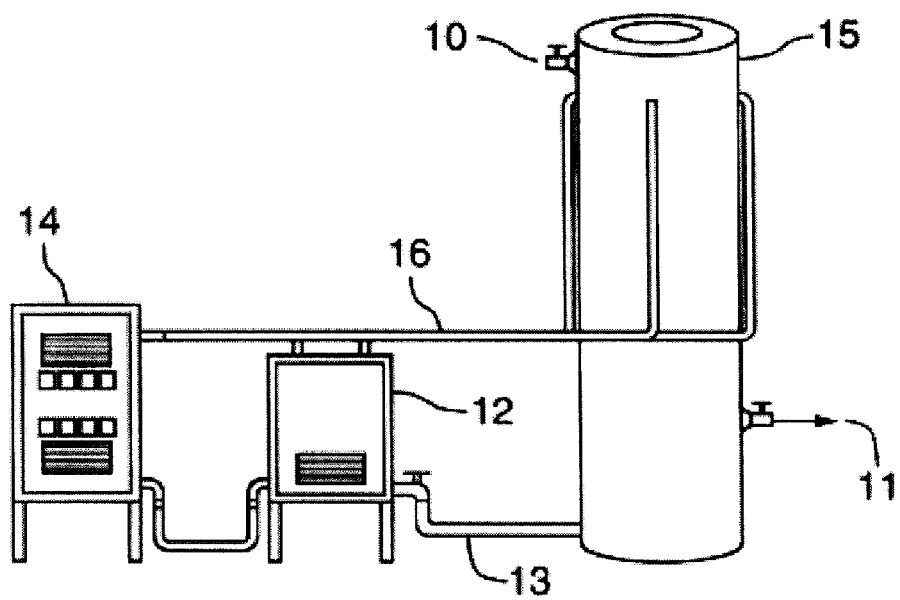
FIG. 4 is a schematic view of a second embodiment also using the method of the invention applied to a liquid electrolytic reaction within a cylindrical reaction chamber.

FIG. 4 shows an alternative version wherein a reaction tower 15 is utilised for the electrolysis reaction. In this second device, utilising the method of the invention, fresh liquid electrolyte enters inlet 10 and reacted electrolyte is removed via outlet 11. A chiller unit 12 maintains optimum electrolyte temperature for the reaction as electrolyte is removed via the base pipe 13, proceeds through the chiller 12 and then through the process unit 14. The process unit 14 houses the frequency generator 2, electrolytic cells 6, standing wave antenna 3 and all related components in a single compact unit. Reacted electrolyte is returned to the tower 15 via return pipe 16. Gases and other reaction products may be removed within the tower 15 and reacted electrolyte removed for further processing via outlet 11.

To recap therefore, the method of the invention creates catalytic action within a chemical reaction by means of induced radio frequency energy to replace the metallic catalyst. The conventional method of producing hydrogen gas from water and then electrolysis process is to pass the water through an electrolytic cell comprising a titanium anode and cathode plated with platinum as the catalyst. As water flows through the electrolytic cell, a stream of electrons in the form of direct electrical current pass through the water between the cathode and anode. With the platinum present in the electrolytic cell, the reaction causes a breakdown in the bond between the hydrogen and oxygen atoms. The hydrogen atoms are liberated as $H_2$ gas at the cathode and are released into the atmosphere or collected after exiting the electrolytic cell. The oxygen atoms that are separated from the hydrogen in the water molecules then collect at the anode and then carried off by the water as dissolved oxygen gas. If the platinum catalyst is not present in the electrolytic cell, this reaction will not be complete and no dissolved oxygen can be measured in the exit stream. As well, no hydrogen gas is measured exiting from the outlet stream. In a conventional reaction therefore, the platinum catalyst is absolute essential for production of these gases.

In contrast, the invention provides a method wherein an electrolysis reaction is conducted in a similar electrolytic cell with the important difference that no platinum plating is provided on either electrode. Conventional wisdom would dictate that electrolytic reaction cannot occur in such circumstances. However, when a radio frequency energy is provided in the electrolyte cell in the range of 9.29 megahertz, dissolved oxygen is in fact measured by a submerged dissolved oxygen probe in the stream after it exits the electrolytic cell. The radio frequency of 9.29 megahertz matches the frequency signal of platinum as measured by conventional nuclear magnetic resonance and as conventionally listed in NMR tables. The introduction of this radio frequency into the reaction by means of a submerged antenna artificially creates catalytic action in an otherwise catalyst-free chemical reaction.

When no radio frequency signal is introduced into this electrolytic cell, very little measure of dissolved oxygen is present in the exit stream. When the radio signal is introduced and fined tuned for frequency and signal strength, the dissolved oxygen meter reads increasing levels of dissolved oxygen until an optimum frequency and amplitude is reached. The result of utilising the method of the invention indicates that the presence of an appropriate radio frequency replaces the physical presence of any metallic catalyst in the reaction. Using the known signal frequency of 9.29 megahertz for platinum as determined by nuclear magnetic resonance, as the starting point for fine tuning an adjustable signal gives an immediate increase in the dissolved oxygen content of the exit stream. Further fine tuning of the frequency strength of the signal improves the production of dissolved oxygen until an optimum combination of frequency and signal strength is discovered by experimentation. Use of radio frequency as opposed to physical presence of actual platinum within the electrolytic cell, reduces the cost of cell manufacture and creates higher dissolved oxygen content in the oxygenated water producer by the electrolytic cell.

TEST EXAMPLE

An experiment was conducted utilising the method of the invention as follows. Water is pumped through the piping 1 and electrolytic cell 6. Direct current power supply is connected to the cathodes and anodes 9 and 8 and sends a stream of electrons through the water between the anode 8 and cathode 9 of the electrolytic cell 6. The frequency generator 2 supplies a selected frequency signal through the submerged antenna 3 upstream of the cell 6. The dissolved oxygen content of the exit stream from the cell is measured via a submerged probe connected to a dissolved oxygen meter. No platinum catalyst is present in the electrolytic cell 6. In contrast, a conventional electrolytic cell would include catalysts plated on the cathode. With the frequency generator off, the flow of input water is measured for dissolved oxygen content, typical results are in the order of 7 milligrams per litre (mg/l). Power is applied to the electrolytic cell 6 by DC power supply and the exit stream of water is measured again for dissolved oxygen content. A typical reading is only marginally higher in the order of 7.6 to 8.5 mg/l. However, when the frequency signal is applied at 9.29 megahertz and signal strength is set at 0.5 watts, the dissolved oxygen reading increases to the order of 14 mg/l.

Further increasing the signal strength to 1.05 watts and fine tuning the frequency of the signal in the order of 9.29 megahertz, increases the dissolved oxygen reading to over 20 mg/l typically.

When the frequency generator 2 is switched off, the dissolved oxygen reading reverts to the 7.6 to 8.5 mg/l range. Switching the frequency generator 2 back on raises the dissolved oxygen reading back up to the 20 mg/l range.

An additional means to create a frequency signal within an electrolytic cell (with the intent to simulate the frequency signal of a known catalyst in the reaction without physical presence of a metallic catalyst) is to oscillate the voltage of a DC power supply connected to the anode and cathode instead of providing a separate radio frequency.

In this second embodiment of the method the voltage is supplied from a DC power supply oscillated within a selectable range to create a sine wave frequency within the electric current and supply to the electrolytic cell anode and cathode. When the current travels from the positive electrode to the negative electrode through the liquid electrolyte, the voltage oscillation frequency can be adjusted to perform the function of the metallic catalyst normally plated onto one or both electrodes. The function of oscillating the voltage at a known frequency accomplishes the identical result as explained above in simulating the frequency signature of a catalyst. Therefore, instead of providing a separate standing wave antenna with variable frequency generator, the second embodiment merely oscillates the voltage slightly at a chosen frequency in a like manner.

Although the above description and accompanying drawings relate to specific preferred embodiments as presently contemplated by the inventor, it will be understood that the invention in its broad aspect includes equivalents of the method steps and elements described and illustrated.

The embodiments of the invention in which an exclusive property or privilege is claimed are defined as follows:

1. A method of using radio frequency waves to imitate the presence of a catalyst and artificially create catalytic action in a catalyst-free chemical reaction involving a substance, the method comprising:
   transmitting radio frequency waves through said substance a reaction mixture at a signal strength sufficient to electronically reproduce the effect of the physical presence of a selected catalyst,
   wherein the radio frequency waves have a selected transmission frequency substantially equal to the signal frequency of said selected catalyst as determined by nuclear magnetic resonance.

2. A method according to claim 1 comprising:
   fine tuning the transmission frequency while monitoring the reaction to optimise the reaction.

3. A method according to claim 1 comprising:
   fine tuning the signal strength while monitoring the reaction to optimise the reaction.

4. A method according to claim 1 wherein the catalyst-free chemical reaction is electrolysis carried out within an electrolytic cell comprising: a cathode; and an anode each communicating with a source of electrical current and each immersed in said substance which is an electrolyte.

5. A method according to claim 4 wherein the radio frequency waves are transmitted via a standing wave antennae submerged in the electrolyte.

6. A method according to claim 5 wherein the electrolytic cell is housed within a conduit and the electrolyte is pumped through the conduit.

7. A method according to claim 6 further including the step of regulating temperature of the electrolyte to optimise the reaction.

8. A method according to claim 6 wherein the electrolyte is water and the reaction comprises electrolysis to increase the dissolved oxygen gas within the water.

9. A method according to claim 8 further including the step of monitoring the dissolved oxygen concentration of the water passed from the electrolytic cell.

10. A method according to claim 1 wherein the selected catalyst is selected from the group consisting of: platinum; rhenium; iridium; and ruthenium.

11. A method according to claim 10 wherein the selected catalyst is platinum and the transmission frequency is in the order of 9.29 megahertz.

12. A method of using radio frequency waves to imitate the presence of an inert metallic catalyst and artificially create catalytic action in a catalyst-free chemical reaction involving a substance, said method comprising:

transmitting radio frequency waves through said substance at a signal strength sufficient electronically to reproduce the effect of the physical presence of a selected inert metallic catalyst, wherein the radio frequency waves have a selected transmission frequency substantially equal to the signal frequency of said selected inert metallic catalyst as determined by nuclear magnetic resonance.

13. The method according to claim 12 comprising:

fine tuning the transmission frequency while monitoring the reaction to optimize the reaction.

14. The method according to claim 12 comprising:

fine tuning the signal strength while monitoring the reaction to optimize the reaction.

15. The method according to claim 12, wherein the catalyst-free chemical reaction is electrolysis carried out within an electrolytic cell comprising a cathode and an anode, each communicating with a source of electrical current and each immersed in said substance which is an electrolyte.

16. The method according to claim 15, wherein the radio frequency waves are transmitted via a standing wave antennae submerged in the electrolyte.

17. The method according to claim 16, wherein the electrolytic cell is housed within a conduit and the electrolyte is pumped through the conduit.

18. The method according to claim 17, further including the step of regulating temperature of the electrolyte to optimize the reaction.

19. The method according to claim 17, wherein the electrolyte is water and the reaction comprises electrolysis to increase the dissolved oxygen gas within the water.

20. The method according to claim 19, further including the step of monitoring the dissolved oxygen concentration of the water passed from the electrolytic cell.

21. The method according to claim 12, wherein the selected inert metallic catalyst is a member selected from the group consisting of platinum, rhenium, iridium, and ruthenium.

22. The method according to claim 21, wherein the selected inert metallic catalyst is platinum and the transmission frequency is in the order of 9.29 megahertz.

* * * * *